United States Patent [19]

Trabelsi et al.

[11] Patent Number: 6,160,161
[45] Date of Patent: Dec. 12, 2000

[54] PER(POLY)FLUORINATED POLYOXYETHYLATED CARBAMATES

[75] Inventors: Hédi Trabelsi, Nice, France; Wolfgang Roehlke, Ulm; Peter Reuter, Laupheim, both of Germany; Massimo Napoli, Padua, Italy; Philippe Lucas, Nice, France; Kenneth Charles Lowe, Nottingham, United Kingdom; Giampaolo Gambaretto, Padua, Italy; Ralf-Peter Franke, Dornstadt, Germany; Carl Martin Edwards, Nottingham, United Kingdom; Lino Conte, Padua, Italy; Aime Cambon, Nice, France

[73] Assignee: F2 Chemicals Limited, United Kingdom

[21] Appl. No.: 09/214,159

[22] PCT Filed: Jun. 24, 1997

[86] PCT No.: PCT/GB97/01704

§ 371 Date: Mar. 5, 1999

§ 102(e) Date: Mar. 5, 1999

[87] PCT Pub. No.: WO97/49675

PCT Pub. Date: Dec. 31, 1997

[30] Foreign Application Priority Data

Jun. 24, 1996 [MC] Monaco ........................................ 2351

[51] Int. Cl.⁷ .................................................. C08G 18/71
[52] U.S. Cl. .......................... 560/161; 560/160; 560/184; 560/167; 528/49; 528/69; 528/70
[58] Field of Search ................................... 560/161, 160, 560/184, 167; 528/49, 69, 70

[56] References Cited

U.S. PATENT DOCUMENTS 4,461,717 7/1984 Moore ..................................... 252/312
4,942,164 7/1990 Baum ...................................... 528/70

FOREIGN PATENT DOCUMENTS 433822 6/1991 European Pat. Off. .
2615187 11/1988 France .
1517024 7/1978 United Kingdom .

*Primary Examiner*—Rachel Gorr
*Attorney, Agent, or Firm*—Klarquist Sparkman Campbell Leigh & Whinston, LLP

[57] ABSTRACT

Per(poly)fluorinated polyoxyethylated carbamates of general formula (I) in which $R_F$ represents a perfluorinated group containing between 1 and 18 carbon atoms, W represents an oxo group or nothing, n is an integer from 1 to 10, m is from values 2 to 6, 80 or not defined, R is an alkyl group, $R_FW(CH_2)_{n+1}NHC(O)$— in which $R_F$ and W are as defined above, —$(CHCH_3CH_2O)_{30}(CH_2CH_2)_{80}C(O)NH(CH_2)_{n+1}R_F$ in which $R_F$ is a perfluorinated group containing from 1 to 18 carbon atoms, R' is a hydrogen atom, an alkyl group containing between 1 and 18 carbon atoms which is optionally substituted, an optionally substituted aryl or aralkyl group, an allyl, methallyl or propargyl group or a perfluorinated chain having between 1 and 18 carbon atoms. These compounds can be used as anti-thrombosis agents or as surfactants or cosurfactants for phospholipids intended for the preparation or stabilization of fluorocarbon emulsions, notably emulsions for biomedical applications.

11 Claims, No Drawings

PER(POLY)FLUORINATED POLYOXYETHYLATED CARBAMATES

The invention relates to the synthesis of new per(poly) fluorinated polyoxyethylated carbamates. These compounds can be used as surfactants or co-surfactants for phospholipids intended for the preparation or stabilisation of fluorocarbon emulsions, notably emulsions for biomedical applications.

Non-ionic fluorinated surfactants are currently used in various fields of application, such as fire-fighting, the plastics, rubber and petroleum industries, in the treatment of textiles, leather, paintings, pigments and coatings, mining and metallurgy, agriculture and silviculture, photography and the graphic arts, in biomedicine to deactivate coated viruses and thus in the preparation of blood products without substantial denaturation of the plasma proteins etc.

Although in some cases it is possible to content oneself with mixtures of polyoxyethylated surfactants [J. Am. Chem. Soc. 106 (1984) 6162], the finer applications (emulsions, microemulsions, gels etc.) occasionally demand homogeneous compounds with perfectly defined structure and of great purity, thus numerous monodisperse detergents have been developed despite their high cost. In particular may be cited:

polyoxyethylated alcohols with the formula: $R_F(CH_2)_pW$ (OH), where p is generally less than 3, $R_F$ is a perfluorinated chain, W designates a chain of oxyethylene units ($OC_2H_4$), where one or more oxygen atoms may be replaced by sulphur atoms, are described in FR-A-2,565,226; $R_FC_2H_4S(C_2H_4O)_mC_2H_4(C_2H_4O)_nH$ presenting oxyethylene and thioethyl groups which can be put together as desired and the number of which can be controlled accurately [Tenside Surf. Det. 31 51994) 124]; $C_nF_{2n+1}CH_2O(C_2H_4O)_mH$ which are excellent emulsifiers of fluorocarbons [EP-A-0051526; Tetrahedron, 39, (1983) 1313; J. Am. Chem. Soc., 106 (1984 6162; Langmuir, 10 (1994) 2131].

polyoxyethylated amides of the formulae: $R_FCONHC_2H_4O)_mH$ [J. Fluorine Chem., 34 (1987) 385; $R_F(CH_2)_nCONH(C_2H_4O)_MH$ [J. Chem. Research. (S), (1984) 292: J. Chem. Research (M), (1984) 2672], $R_FC_2H_4NHCOC(CH_2OH)_2CH_3$ [J. Chem. Soc., Chem. Commun., (1991) 863], $R_FC_2H_4CH(CONH(C_2H_4O)_mH)_2$ (MC Patent No 2334 1996)], the product sold under the trade mark XMO-10 with the formula $C_3F_7O(CF_2)_3CONH(CH_2)_3N(O)(CH_3)_2$ [Prog. Clin. Biol. Res., 122 (1983) 169]; $R_F(CH_2)_pC(O)N[OC_2H_4)_nMe]_2$ where p is generally less than 3. Products of this family where p=1 or 0 are described in French Patent Application No 87.06515.

polyoxyethylated ethers with the formula $R_F(CH_2)_pQ(C_2H_4O)_nMe$ where p is less than 5, in which $R_F$ is a perfluorinated chain and Q designates groups such as —$O(CH_2)_4O$—, —$O(CH_2)_3C(O)O$—, —$CH(OEt)CH_2O$— [Biomat., Art. Cells, Biotech., 20 (1992) 115; J. Fluorine Chem., 68 (1994) 221].

polyfluorinated polyoxyethylated amines with the formula $R_FC_2H_4N[(C_2H_4O)_mR]_2$ where m is 2 or 3, $R_F$ is a perfluorinated chain and R represents a hydrogen atom or a methyl group [J. Colloid Interface Sci., 177 (1996) 101].

perfluorinated glycosidic compounds used notably in the extraction and purification of membrane proteins [New J. Chem., 1994, 18, 839] or in the preparation of organised systems [Carbohydrates as Organic Raw Materials, Verlagsgesellschaft. (Ed), Weinheim, (1993) 209–259: Organofluorine Compounds in Medicinal Chemistry and Biomedical Applications R Filler et al (Eds), Elsevier, (1993) 339–380].

This invention relates to the use of per(poly)fluorinated polyoxyethylated carbamates as anti-thrombosis agents or as a surfactant or as a co-surfactant for, in particular, phospholipids, especially of egg yolk, to produce or stabilise emulsions, especially fluorocarbon emulsions intended, for example, for a biomedical application, for example as injectable oxygen transporters (called "blood substitutes"). The general formula for these carbamates is:

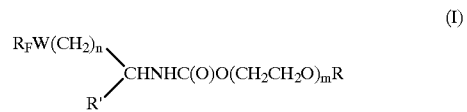

(I)

in which $R_F$ represents a perfluorinated group containing between 1 and 18 carbon atoms, W represents an oxo group or nothing, n is an integer from 1 to 10, m is from 2 to 6, 80 or not defined, R is an alkyl group preferably containing between 1 and 4 carbon atoms, $R_FW(CH_2)_{n+1}NHC(O)$— in which $R_F$ and W have the same significance as above, or is —$(CHCH_3CH_2O)_{30}(CH_2CH_2O)_{80}C(O)NH(CH_2)_{n+1}R_F$ in which $R_F$ is a perfluorinated group containing 1 to 18 or preferably 4 to 18 carbon atoms. R' is a hydrogen atom, an alkyl group containing between 1 and 18 carbon atoms which is optionally substituted, an optionally substituted aryl or optionally substituted aralkyl group, an allyl, methallyl or propargyl group or a perfluorinated group with 1 to 18 or preferably 4 to 18 carbon atoms. As substituents which may be present on the alkyl, aryl or aralkyl radicals, the hydroxyl or mercapto groups may be cited. As the perfluorinated groups may be mentioned perfluoroaliphatic groups, for example perfluoroalkyl; the perfluorinated groups may be branched but in one class of compounds are straight chain.

We have found that the invention enables the provision of components which display a fairly good level of biological tolerance and do not cause haemolysis of red blood cells.

In one class of compounds. W is nothing. In another class, n is from 1 to 4. A further class of compounds contain an $R_F$ group which is a linear perfluorinated group containing 4, 6, 8 or 10 carbon atoms. A preferred class of compounds contains all three of the aforesaid features.

A yet further class of compounds are those compounds in which R' is hydrogen. In another class of compounds, R' is a said R' group other than hydrogen.

In one class of compounds W is oxo and $R_F$ is optionally a linear perfluorinated group containing 1, 3, 4, 5, 6, 7, 8 or 10 carbon atoms.

Another class of compounds have an R group which is alkyl.

In general, the compounds of the invention are easily prepared by condensation of oligoethylenes with per(poly) fluoroalkylated isocyanates with satisfactory yields. So, for example, the compounds of the invention in which W is nothing, n is between 1 and 10, m is from 2 to 6 or not defined, R is an alkyl group preferably containing between 1 and 4 carbon atoms, R' is a hydrogen atom and $R_F$ a perfluorinated aliphatic chain preferably comprising 4 to 18 carbon atoms, ie formula (II) compounds:

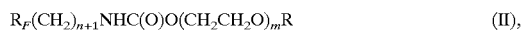

are formed quantitatively by the action of polyfluoroalkylated isocyanates on the oligo- or poly-ethylenes. The reaction is best conducted in an anhydrous atmosphere at a temperature of between 60 and 70° C. for a period of 30 to 48 hours. The synthesis of the isocyanates used as starting compounds has been described [MC Patent No 2349 (1996), J. Fluorine Chem. 56 (1992) 85].

As non-restrictive examples of partially protected oligoethylenes used, in particular there may be cited the following oligooxyethylenes: monomethyl ether of diethylene glycol, monoethyl ether of diethylene glycol, monomethyl ether of triethylene glycol or monomethyl ethers of polyethylene glycol (which are commercial products) or monomethyl ether of tetraethylene glycol, monomethyl ether of pentaethylene glycol and monomethyl ether of hexaethylene glycol, the preparation of which has been described recently [Langmuir, 10 (1994) 2136]. However, the action of the monomethyl ethers of polyethylene glycol on the isocyanates makes it possible to obtain polydisperse surfactant compounds.

Oligoethylenes such as tetraethylene glycol and pentaethylene glycol behave in the same way towards the above-mentioned isocyanates and provide formula (III) or formula (IV) dicarbamates.

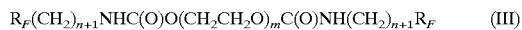
(III)

or

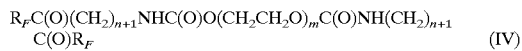
(IV)

in which $R_F$, n and m may be as defined in relation to Formula (I) and $R_F$ preferably represents a perfluorinated group containing between 4 and 18 carbon atoms, n is from 1 to 10 and m is preferably 4 or 5. These compounds may be obtained by reacting two moles of isocyanate or, as the case may be, oxoisocyanate with one mole of oligoethylene. In one class of Formula (III) compounds n is from 1 to 4; in another class $R_F$ is a linear perfluorinated group containing 4, 6, 8 or 10 carbon atoms. Some Formula (III) compounds belong to both classes. In one class of Formula (IV) compounds $R_F$ is a linear perfluorinated group containing 1, 3, 4, 5, 6, 7, 8 or 10 carbon atoms; in another class m is 3 or 4. Some Formula (IV) compounds belong to both classes. A further class of Formula (III) and (IV) compounds comprises compounds in which n is 3 or 4 and/or m is 4 or 5.

The synthesis of the oxoisocyanates used as starting products for Formula (IV) compounds has been described already [MC Patent No 2350 (1996) and the PCT application claiming priority therefrom, filed on Jun. 24, 1997 under the title "Synthesis of Glycosidic Perfluoroaliphatic Surface-Active Agents by F2 Chemicals Ltd et al, which PCT application is included herein by reference].

By using Pluronic F-68 (commercial product, mp=54° C.) polydisperse surfactant compounds with the formula (V) are obtained.

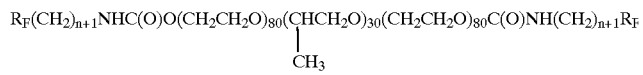

in which n is an integer from 1 to 10 and $R_F$ is a perfluorinated group preferably containing between 4 and 18 carbon atoms. These compounds are prepared by the action of polyfluoroalkylated isocyanates on an excess of Pluronic F-68. In one class of Formula (V) compounds n is from 1 to 4; in another class $R_F$ is a linear perfluorinated group containing 4, 6, 8 or 10 carbon atoms. Some Formula (V) compounds belong to both classes.

The use of isocyanates differently substituted with the partially protected oligoethylenes gives rise to carbamates with the formula (VI).

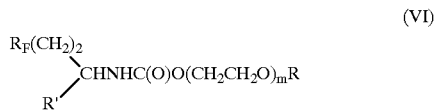
(VI)

in which $R_F$ represents a perfluorinated group preferably containing between 4 and 18 carbon atoms, m takes the values 2 to 6 or not defined, R is an alkyl group preferably containing between 1 and 4 carbon atoms and R' represents an optionally substituted alkyl group containing between 1 and 18 carbon atoms, an optionally substituted aralkyl radical, an allyl, methallyl or propargyl radical or a perfluorinated chain preferably having 4 to 18 carbon atoms. As possible substituents present on the alkyl, aryl or aralkyl radicals, the hydroxyl or mercapto groups may be cited.

The reaction may be performed in an anhydrous atmosphere at a temperature of, for example, between 60 and 70° C. for a period of 30 to 48 hours. The branched isocyanates used as starting compounds are described [MC Patent No 2349 (1996)].

Formula (I) compounds in which W is an oxo group, n is an integer of 1 to 4 (preferably 3 or 4), m is preferably from 2 to 6 or a number which is not defined, R' is a hydrogen atom, R is an alkyl group preferably containing between 1 and 4 carbon atoms and $R_F$ represents a perfluorinated group containing between 1 and 18 carbon atoms (1, 3, 4, 5, 6, 7, 8 or 10 carbon atoms in one class of compounds), ie formula (VII) compounds:

(VII)

are obtained by the condensation of partially protected oligoethylenes on the perfluoroalkylated oxoisocyanates.

The compounds of formulae (II)–(VII) and their subclasses are each distinct classes of compounds of the invention.

The following Examples illustrate this invention without in any way limiting it.

EXAMPLE 1.

Preparation of carbamates of the formula

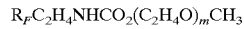

where m=2 or 3.

An equimolar mixture of 2-F-alkylethyl isocyanate and monomethyl ether of diethylene glycol (or monomethyl ether of triethylene glycol) is heated to 65° C. for approximately 48 hours. It is then cooled to ambient temperature. The carbamate formed is purified under a column of silica gel, eluant: ethyl acetate/petroleum ether: 5/5.

By way of example we give the yields and characteristics of some compounds:

No.1. $C_6F_{13}C_2H_4NHCO_2(C_2H_4O)_2CH_3$ Yield=90% viscous liquid

Surface tension (0.1%, 25° C.)=19.3 mN/m.
I.R. (vcm$^{-1}$): 3332, 2878, 1719, 1300-1100 NMR of proton (CDCl$_3$/TMS): 2.40 (m, 2H, R$_F$CH$_2$); 3.4 (s, 3H, OCH$_3$); 3.7 (m, 8H, (C$_2$H$_4$O)$_2$); 4.2(t, J=4.5 Hz, 2H, CH$_2$N); 5.2 (t, J=5.4 Hz, 1H, NH) NMR of fluorine (CDCl$_3$/CCl$_3$F): −81 (3F, CF$_3$); −114.5 (2F, CF$_2$); −122 (2F,CF$_2$); −123 (2F,CF$_2$); −124 (2F, CF$_2$); −127 (2F,CF$_2$).

No.2. C$_6$F$_{13}$C$_2$H$_4$NHCO$_2$(C$_2$H$_4$O)$_3$CH$_3$ Yield=90% liquid
Surface tension (0.1%, 25° C.)=15.9 mN/m.
I.R. (vcm$^{-1}$): 3332, 2878, 1719, 1300-1100 NMR of proton (CDCl$_3$/TMS): 2.40 (m, 2H, R$_F$CH$_2$); 3.4 (s, 3H, OCH$_3$); 3.7 (m, 12H, (C$_2$H$_4$O)$_3$); 4.2 (t, J=4.5 Hz, 2H, CH$_2$N); 5.2 (t, J=5.4 Hz, 1H, NH) NMR of fluorine (CDCl$_3$/CCl$_3$F): −81 (3F,CF$_3$); −115 (2F, CF$_2$); −122 (2F,CF$_2$); −123 (2F,CF$_2$); −124 (2F, CF$_2$); −127 (2F,CF$_2$).

No.3. C$_8$F$_{17}$C$_2$H$_4$NHCO$_2$(C$_2$H$_4$O)$_2$CH$_3$ Yield=90% white solid
m.p.=40° C., b.p.=140° C./0.02 mm Hg,
Surface tension (0.1%, 25° C.)=18.6 mN/m.
I.R. (vcm$^{-1}$): 3322, 2878, 1697, 1300-1100 NMR of proton (CDCl$_3$/TMS): 2.40 (m, 2H, R$_F$CH$_2$); 3.4 (s, 3H, OCH$_3$); 3.7 (m, 8H, (C$_2$H$_4$O)$_2$); 4.2 (t, J=4.5 Hz, 2H, CH$_2$N); 5.2 (t, J=5.4 Hz, 1H, NH) NMR of fluorine (CDCl$_3$/CCl$_3$F): −81 (3F,CF$_3$); −114 (2F, CF$_2$); −122 (6F,CF$_2$); −123 (2F,CF$_2$); −124 (2F,CF$_2$); −126 (2F, CF$_2$)

No.4. C$_8$F$_{17}$C$_2$H$_4$NHCO$_2$(C$_2$H$_4$O)$_3$CH$_3$ Yield=85% liquid
Surface tension (0.1%, 25° C.)=15.1 mN/n.
I.R. (vcm$^{-1}$): 3322, 2878, 1698, 1300-1100 NMR of proton (CDCl$_3$/TMS): 2.40 (m, 2H, R$_F$CH$_2$); 3.4 (s, 3H, OCH$_3$); 3.7 (m, 12H, (C$_2$H$_4$O)$_3$); 4.2 (t, J=4.5 Hz, 2H, CH$_2$N); 5.2 (t, J=5.4 Hz, 1H, NH) NMR of fluorine (CDCl$_3$/CCl$_3$F): −81 (3F,CF$_3$); −114 (2F, CF$_2$) −122 (6F,CF$_2$); −123 (2F,CF$_2$); −124 (2F, CF$_2$); −126 (2F,CF$_2$)

EXAMPLE 2.
Preparation of carbamates with the formula
R$_F$C$_3$H$_6$NHCO$_2$(C$_2$H$_4$O)$_m$CH$_3$ where m=2 or 3. The procedure is as above (example 1), replacing 2-F-alkylethyl isocyanate with 3-F-alkylpropyl isocyanate. The raw products formed are then purified on a silica column, eluant: diethyl ether oxide/petroleum ether (5/5).

By way of example we give the yields and characteristics of some compounds:

No.1. C$_4$F$_9$C$_3$H$_6$NHCO$_2$(C$_2$H$_4$O)$_2$CH$_3$ Yield=90% liquid
Surface tension (0.1%, 25° C.)=19.3 mN/ m.
I.R. (vcm$^{-1}$): 3335, 2878, 1730, 1300-1100 NMR of proton (CDCl$_3$/TMS): 1.80 (m, 2H, C$_4$F$_9$CH$_2$CH$_2$); 2.20 (m, 2H, R$_F$CH$_2$); 3.4 (s, 3H, OCH$_3$); 3.7 (m, 8H, (C$_2$H$_4$O)$_2$); 4.2 (t, J=4.5 Hz, 2H, CH$_2$N); 5.1 (t, J=5.4 Hz, 1H, NH) NMR of fluorine (CDCl$_3$/CCl$_3$F): −81 (3F,CF$_3$); −115 (2F, CF$_2$); −124 (2F,CF$_2$); −126 (2F,CF$_2$)

No.2. C$_6$F$_{13}$C$_3$H$_6$NHCO$_2$(C$_2$H$_4$O)$_2$CH$_3$ Yield=87% liquid
Surface tension (0.1%, 25° C.)=19.4 mN/m.
I.R. (vcm$^{-1}$): 3344, 2878, 1729, 1300-1100 NMR of proton (CDCl$_3$/TMS): 1.80 (m, 2H, C$_6$F$_{13}$CH$_2$CH$_2$); 2.20 (m, 2H, R$_F$CH$_2$); 3.4 (s, 3H, OCH$_3$); 3.7 (m, 8H, (C$_2$H$_4$O)$_2$); 4.2 (t, J=4.5 Hz, 2H, CH$_2$N); 5.1 (t, J=5.4 Hz, 1H, NH) NMR of fluorine (CDCl$_3$/CCl$_3$F): −81 (3F,CF$_3$); −115 (2F, CF$_2$); −122 (2F,CF$_2$); −123 (2F,CF$_2$); −124 (2F, CF$_2$); −127 (2F, CF$_2$).

No.3. C$_6$F$_{13}$C$_3$H$_6$NHCO$_2$(C$_2$H$_4$O)$_3$CH$_3$ Yield=90% liquid
Surface tension (0.1%, 25° C.) =16.1 mN/m.
I.R. (vcm$^{-1}$): 3334, 2878, 1721, 1300-1100 NMR of proton (CDCl$_3$/TMS): 1.80 (m, 2H, C$_6$F$_{13}$CH$_2$CH$_2$); 2.20 (m, 2H, R$_F$CH$_2$); 3.4 (s, 3H, OCH$_3$); 3.6 (m, 12H, (C$_2$H$_4$O)$_3$); 4.2 (t, J=4.5 Hz, 2H, CH$_2$N); 5.1 (t, J=5.4 Hz, 1H, NH) NMR of fluorine (CDCl$_3$/CCl$_3$F): −81 (3F,CF$_3$); −115 (2F, CF$_2$); −122 (2F,CF$_2$); −123 (2F,CF$_2$);−124 (2F, CF$_2$); −127 (2F, CF$_2$)

No.4. C$_8$F$_{17}$C$_3$H$_6$NHCO$_2$(C$_2$H$_4$O)$_2$CH$_3$ Yield=90% liquid
Surface tension (0.1%, 25° C.)=15.8 mN/m.
I.R. (vcm$^{-1}$): 3334, 2878, 1715, 1300-1100 NMR of proton (CDCl$_3$/TMS): 1.80 (m, 2H, C$_8$F$_{17}$CH$_2$CH$_2$); 2.20 (m, 2H, R$_F$CH$_2$); 3.4 (s, 3H, OCH$_3$); 3.7 (m, 8H, (C$_2$H$_4$O)$_2$); 4.2 (t, J=4.5 Hz, 2H, CH$_2$N); 5.1 (t, J=5.4 Hz, 1H, NH) NMR of fluorine (CDCl$_3$/CCl$_3$F): −81 (3F,CF$_3$); −114 (2F, CF$_2$); −122 (6F, 3 CF$_2$); −123 (2F,CF$_2$); −124 (2F, CF$_2$); −127 (2F,CF$_2$).

No.5. C$_8$F$_{17}$C$_3$H$_6$NHCO$_2$(C$_2$H$_4$O)$_3$CH$_3$ Yield=90% pasty product
Surface tension (0.1%, 25° C.) =15.3 mN/m.
I.R. (vcm$^{-1}$): 3335, 2878, 1730, 1300-1100 NMR of proton (CDCl$_3$/TMS): 1.80 (m, 2H, C$_8$F$_{17}$CH$_2$CH$_2$); 2.20 (m, 2H, R$_F$CH$_2$); 3.4 (s, 3H, OCH$_3$); 3.7 (m, 12H, (C$_2$H$_4$O)$_3$); 4.2 (t, J=4.5 Hz, 2H, CH$_2$N); 5.1 (t, J=5.4 Hz, 1H, NH) NMR of fluorine (CDCl$_3$/CCl$_3$F): −81 (3F,CF$_3$); −114.5 (2F, CF$_2$); −122 (6F, 3 CF$_2$); −123 (2F,CF$_2$); −124 (2F,CF$_2$); −127 (2F,CF$_2$).

EXAMPLE 3.
Preparation of carbamates with the formula:

R$_F$C$_2$H$_4$NHCO$_2$(C$_2$H$_4$O)$_m$C(O)NHC$_2$H$_4$R$_F$ where m=4 or 5.

The procedure is as above (example 1). The raw products formed by the condensation of 0.002 of a mole of 2-F-alkylethyl isocyanate with 0.001 of a mole of oligoethylene are then purified by recrystallization in chloroform.

By way of example we give the yields and characteristics of some compounds:

No.1. C$_8$F$_{17}$C$_2$H$_4$NHCO$_2$(C$_2$H$_4$O)$_4$C(O)NHC$_2$H$_4$C$_8$F$_{17}$
Yield=85% white solid
m.p.=75°, very slightly soluble in water.
NMR of proton (acetone d$_6$/TMS): 2.50 (m, 4H, 2×R$_F$CH$_2$); 3.6 (m, 16H, (C$_2$H$_4$O)$_4$); 4.2 (t, J=4.6 Hz, 4H, CH$_2$N); 6.6 (t, J=5.4 Hz, 2H, NH) NMR of fluorine (acetone d$_6$/CCl$_3$F): −81 (CF$_3$); −114 (CF$_2$): −122 (3 CF$_2$); −123 (CF$_2$); −124 (CF$_2$); −127 (CF$_2$).

No.2. C$_8$F$_{17}$C$_2$H$_4$NHCO$_2$(C$_2$H$_4$O)$_5$C(O)NHC$_2$H$_4$C$_8$H$_{17}$
Yield 85% white solid
m.p.=67° C. very slightly soluble in water.
NMR of proton (acetone d$_6$/TMS): 2.50 (m, 4H, R$_F$CH$_2$); 3.6 (m, 20H, (C$_2$H$_4$O)$_5$); 4.2 (t, J=4.6 Hz, 4H, CH$_2$N); 6.5 (t, J=5.4 Hz, 2H, 2×NH)
NMR of fluorine (acetone d$_6$/CCl$_3$F): −81 (CF$_3$); −114 (CF$_2$); −122 (3 CF$_2$); −123 (CF$_2$); −124 (CF$_2$); −127 (CF$_2$).

EXAMPLE 4.
Preparation of carbamates with the formula:

R$_F$C$_2$H$_4$CH(R')NHCO$_2$(C$_2$H$_4$O)$_3$CH$_3$ where m=2 or 3.
The procedure is as above (example 1), replacing 2-F-alkylethyl isocyanate with a ramified isocyanate. The raw products formed are then purified on a silica column.
eluant: ethyl acetate/Methanol 9:1.

By way of example we give the yields and characteristics of some compounds:

No.1. C$_4$F$_9$C$_2$H$_4$CH[CH$_3$(CH$_2$)$_{10}$]NHCO$_2$(C$_2$H$_4$O)$_3$CH$_3$
Yield=90% liquid Surface tension (0.1%, 25° C.)=29.1 mN/m.
I.R. (vcm$^{-1}$): 3321, 2926, 2854, 1696, 1300-1100 NMR of proton (CDCl$_3$/TMS): 0.9 (t, J=6.48 Hz, 3H, CH$_2$); 1.30 (m, 18H, CH$_3$(CH$_2$)$_9$); 1.6–2.2 (m, 6H, R$_F$CH$_2$CH$_2$, CH$_3$(CH$_2$)$_9$CH$_2$), 3.4 (s, 3H, OCH$_3$); 3.7 (m, 12H, (C$_2$H$_4$O)$_3$); 4.2 (m, 1H, CHNHCO$_2$); 4.7 (m, 1H, NCHO$_2$); NMR of fluorine (CDCl$_3$/CCl$_3$F): −81 (3F,CF$_3$); −115 (2F, CF$_2$); −124(2F, CF$_2$); −126 (2F,CF$_2$).

No.2. C$_6$F$_{13}$C$_2$H$_4$CH[CH$_3$(CH$_2$)$_8$]NHCO$_2$(C$_2$H$_4$O)$_2$CH$_3$
Yield=90% liquid
Surface tension (0.1%, 25° C.)=30.0 mN/m.
I.R. (vcm$^{-1}$): 3320, 2926, 2854, 1697, 1300-1100 NMR of proton (CDCl$_3$/TMS): 0.9 (t, J=6.53 Hz, 3H, CH$_3$); 1.30 (m, 14H, CH$_3$(CH$_2$)$_7$); 1.6–2.2 (m, 6H, R$_F$CH$_2$CH$_2$, CH$_3$(CH$_2$)$_7$CH$_2$), 3.4 (s, 3H, OCH$_3$); 3.7 (m, 8H, (C$_2$H$_4$O)$_2$); 4.2 (m, 1H, CHNHCO$_2$); 4.7 (m, 1H, NCHO$_2$); NMR of fluorine (CDCl$_3$/CCl$_3$F): −81 (3F,CF$_3$); −115 (2F, CF$_2$); −122 (2F, CF$_2$); −123 (2F,CF$_2$); −124(2F,CF$_2$); −127 (2F,CF$_2$).

No.3. C$_6$F$_{13}$C$_2$H$_4$CH[CH$_3$(CH$_2$)$_8$]NHCO$_2$(C$_2$H$_4$O)$_3$CH$_3$
Yield=90% liquid
Surface tension (0.1%, 25° C.)=25.6 mN/m.
I.R. (vcm$^{-1}$): 3318, 2927, 2856, 1694, 1300-1100 NMR of proton (CDCl$_3$/TMS): 0.9 (t, J=6.58 Hz, 3H, CH$_3$); 1.30 (m, 14H, CH$_3$(CH$_2$)$_7$); 1.6–2.2 (m, 6H, R$_F$CH$_2$CH$_2$, CH$_3$(CH$_2$)$_7$CH$_2$), 3.4 (s, 3H, OCH$_3$); 3.7 (m, 12H, (C$_2$H$_4$O)$_3$); 4.2 (m, 1H, CHNHCO$_2$); 4.7 (m, 1H, NCHO$_2$); NMR of fluorine (CDCl$_3$/CCl$_3$F): −81 (3F,CF$_3$); −115 (2F,CF$_2$); −122 (2F, CF$_2$); −123 (2F,CF$_2$); −124 (2F, CF$_2$); −127 (2F,CF$_2$).

No.4. C$_6$F$_{13}$ C$_2$H$_4$CH[CH$_3$(CH$_2$)$_9$]NHCO$_2$(C$_2$H$_4$O)$_2$CH$_3$
Yield=90% liquid
Surface tension (0.1%, 25° C.)=29.0 mN/m.
I.R. (vcm$^{-1}$): 3318, 2927, 2856, 1694, 1300-1100 NMR of proton (CDCl$_3$/TMS): 0.9 (t, J=6.58 Hz, 3H, CH$_3$); 1.30 (m, 16H, CH$_3$(CH$_2$)$_8$); 1.6–2.2 (m, 6H, R$_F$CH$_2$CH$_2$, CH$_3$(CH$_2$)$_8$CH$_2$), 3.4 (s, 3H, OCH$_3$); 3.7 (m, 8H, (C$_2$H$_4$O)$_2$); 4.2 (m, 1H, CHNHCO$_2$; 4.7 (m, 1H, NHCO$_2$); NMR of fluorine (CDCl$_3$/CCl$_3$F): −81 (3F,CF$_3$); −115 (2F,CF$_2$); −122 (2F, CF$_2$); −123 (2F,CF$_2$); −124 (2F,CF$_2$); −127 (2F,CF$_2$).

No.5. C$_6$F$_{13}$C$_2$H$_4$CH[CH$_3$(CH$_2$)$_9$]NHCO$_2$(C$_2$H$_4$O)$_3$CH$_3$
Yield=90% liquid
Surface tension (0.1%, 25° C.) 23.2 mN/m.
I.R. (vcm$^{-1}$) 3318, 2927, 2856, 1694, 1300-1100 NMR of proton (CDCl$_3$/TMS): 0.9 (t, J=6.58 Hz, 3H, CH$_3$); 1.30 (m, 16H, CH$_3$(CH$_2$)$_8$); 1.6–2.2 (m, 6H, R$_F$CH$_2$CH$_2$, CH$_3$(CH$_2$)$_8$CH$_2$); 3.4 (s, 3H, OCH$_3$); 3.7 (m, 12H, (C$_2$H$_4$O)$_3$); 4.2 (m, 1H, CHNHCO$_2$); 4.7 (m, 1H, NHCO$_2$); NMR of fluorine (CDCl$_3$/CCl$_3$F): −81 (3F,CF$_3$); −115 (2F, CF$_2$); −122 (2F, CF$_2$); −123 (2F,CF$_2$); −124 (2F,CF$_2$); −127 (2F,CF$_2$).

No.6. C$_6$F$_{13}$C$_2$H$_4$CH[CH$_3$(CH$_2$)$_{15}$]NHCO$_2$(C$_2$H$_4$O)$_3$CH$_3$
Yield=80% white solid
m.p.=38° C., insoluble in water.
NMR of proton (CDCl$_3$/TMS): 0.9 (t, J=6.52 Hz, 3H, CH$_3$); 1.30 (m, 28H, CH$_3$(CH$_2$)$_{14}$); 1.6–2.2 (m, 6H, R$_F$CH$_2$CH$_2$, CH$_3$(CH$_2$)$_{14}$CH$_2$); 3.4 (s, 3H, OCH$_3$); 3.7 (m, 12H, (C$_2$H$_4$O)$_3$); 4.2 (m, 1H, CHNHCO$_2$); 4.7 (m, 1H, NHCO$_2$); NMR of fluorine (CDCl$_3$/CCl$_3$F): −81 (3F,CF$_3$); −115 (2F,CF$_2$); −122 (2F,CF$_2$); −123 (2F,CF$_2$); −124 (2F,CF$_2$); −127 (2F,CF$_2$).

No.7. C$_8$F$_{17}$C$_2$H$_4$CH[CH$_3$(CH$_2$)$_{11}$]NHCO$_2$(C$_2$H$_4$O)$_3$CH$_3$
Yield=90% pasty solid
Surface tension (0.1%, 25° C.)=20.3 mN/m.
I.R. (vcm$^{-1}$) 3320, 2925, 2855, 1694, 1300-1100 NMR of proton (CDCl$_3$/TMS): 0.9 (t, J=6.58 Hz, 3H, CH$_3$); 1.30 (m, 20H, CH$_3$(CH$_2$)$_{10}$); 1.6–2.2 (m, 6H, R$_F$CH$_2$CH$_2$, CH$_3$(CH$_2$)$_{10}$CH$_2$); 3.4 (s, 3H, OCH$_3$); 3.7 (m, 12H, (C$_2$H$_4$O)$_3$); 4.2 (m, 1H, CHNHCO$_2$); 4.7 (m, 1H, NHCO$_2$); NMR of fluorine (CDCl$_3$/CCl$_3$F): −81 (3F,CF$_3$); −114 (2F,CF$_2$); −122 (6F, CF$_2$); −123 (2F,CF$_2$); −124 (2F,CF$_2$); −127 (2F,CF$_2$)

EXAMPLE 5.
Preparation of the carbamate with the formula:

The procedure is as above (example 1), replacing 2-F-alkylethyl isocyanate with a perfluoroalkylated oxoisocyanate. The raw product formed in this way is then purified by recrystallization in hexane.

C$_7$F$_{15}$C(O)CH$_2$CH$_2$CH$_2$CH$_2$NHCO$_2$(C$_2$H$_4$O)$_2$CH$_3$ Yield= 85% white solid
m.p.=43°, surface tension (0.1%, 25° C.)=16.1 mN/m.
NMR of proton (CDCl$_3$/TMS): 1.60 (m, 4H, C$_2$H$_4$); 2.80 (t, 2H, J=5.4 Hz CH$_2$C(O)); 3.4 (s, 3H, OCH$_3$); 3.7 (m, 8H, (C$_2$H$_4$O)$_2$); 4.2 (t, J=4.5 Hz, 2H, CH$_2$N); 4.8 (t, J=5.4 Hz, 1H, NH) NMR of fluorine (CDCl$_3$/CCl$_3$F): −81 (3F,CF$_3$); −120 (2F,CF$_2$); −121 (2F,CF$_2$); −122.5 (4F,2CF$_2$); −122.8 (2F,CF$_2$); −127 (2F,CF$_2$).

Further aspects of the invention as well as preferred embodiments thereof are set forth in the following claims.

What is claimed is:

1. A per(poly)fluorinated polyoxyethylated carbamate of the general formula:

in which R$_F$ represents a perfluorinated group containing between 1 and 18 carbon atoms, W represents an oxo group or nothing, n is an integer from 1 to 10, m is from values 2 to 6 or 80, R is an alkyl group, R$_F$W(CH$_2$)$_{n+1}$NHC(O)— in which R$_F$ and W are as defined above, —(CHCH$_3$CH$_2$O)$_{30}$ (CH$_2$CH$_2$O)$_{80}$C(O)NH(CH$_2$)$_{n+1}$R$_F$ in which R$_F$ is a perfluorinated group containing from 1 to 18 carbon atoms, R' is a hydrogen atom, an alkyl group containing between 1 and 18 carbon atoms which is optionally substituted, an optionally substituted aryl or aralkyl group, an allyl, methallyl or propargyl group or a perfluorinated chain having between 1 and 18 carbon atoms.

2. A compound of claim 1, in which W is nothing.
3. A compound of claim 1, in which R' is a hydrogen atom.
4. A compound of claim 1, in which R' is an alkyl group containing between 1 and 18 carbon atoms which is optionally substituted, an optionally substituted aryl or aralkyl group, an allyl, methallyl or propargyl radical or perfluorinated chain having from 4 to 18 carbon atoms.
5. A compound of claim 1, in which the optional substituent(s) on the alkyl, aryl or aralkyl groups is/are selected from hydroxyl and mercapto.
6. A compound of claim 1, in which n is from 1 to 4 and/or m is from 2 to 6.
7. A compound of claim 1, in which R contains from 1 to 4 carbon atoms.
8. A compound of claim 1, in which R$_F$ is a linear perfluorinated group containing 4, 6, 8 or 10 carbon atoms.
9. A compound of claim 1, in which R$_f$ is a linear perfluorinated group containing 4, 6, 8, or 10 carbon atoms, n is from 1 to 4, and W is nothing.
10. A compound of claim 1, in which W is an oxo group.
11. A compound of claim 10, in which R$_F$ is a linear perfluorinated group containing 1, 3, 4, 5, 6, 7, 8 or 10 carbon atoms.

* * * * *

UNITED STATES PATENT AND TRADEMARK OFFICE
CERTIFICATE OF CORRECTION

PATENT NO.   : 6,160,161
DATED        : December 20, 2000
INVENTOR(S)  : Trabelsi et al.

It is certified that error appears in the above-identified patent and that said Letters Patent is hereby corrected as shown below:

Title page,
Inventors, "Padua" should read -- Napoli, Gambaretto, and Conte, city of Padova --

Column 5,
Line 29, "15.1 mN/n" should read -- 15.1 mN/m --

Column 7,
Line 35, "CH$_2$), 3.4" should read -- CH$_2$); 3.4 --

Signed and Sealed this

Second Day of July, 2002

Attest:

JAMES E. ROGAN
*Attesting Officer*   *Director of the United States Patent and Trademark Office*